United States Patent
Bouvier et al.

(10) Patent No.: US 7,053,366 B2
(45) Date of Patent: May 30, 2006

(54) DESALTING PLATE FOR MALDI MASS SPECTROMETRY

(75) Inventors: Edouard S. P. Bouvier, Stow, MA (US); Bruce J. Compton, Lexington, MA (US); Dominic O. Gostick, Marlborough, MA (US); Jeffery Mark Brown, Mottram-in-Longdendale via Hyde (GB)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 10/478,399

(22) PCT Filed: May 24, 2002

(86) PCT No.: PCT/US02/16501

§ 371 (c)(1),
(2), (4) Date: Nov. 19, 2004

(87) PCT Pub. No.: WO02/096541

PCT Pub. Date: Dec. 5, 2002

(65) Prior Publication Data

US 2005/0087685 A1    Apr. 28, 2005

Related U.S. Application Data

(60) Provisional application No. 60/293,496, filed on May 25, 2001.

(51) Int. Cl.
*H01J 37/20* (2006.01)
*G01N 1/28* (2006.01)

(52) U.S. Cl. ............... 250/288; 250/281; 250/282; 436/173; 436/174

(58) Field of Classification Search ............... None
See application file for complete search history.

(56) References Cited

U.S. PATENT DOCUMENTS

| 4,527,059 A | 7/1985 | Benninghoven et al. |
| 5,260,571 A | 11/1993 | Cottrell et al. .............. 250/288 |
| 5,281,538 A | 1/1994 | Cottrell et al. .............. 436/173 |
| 5,308,978 A | 5/1994 | Cottrell et al. .............. 250/288 |
| 5,334,310 A | 8/1994 | Frechet et al. .......... 210/198.2 |
| 5,480,526 A | 1/1996 | Liao et al. ............... 204/182.8 |
| 5,595,636 A * | 1/1997 | Franzen ..................... 204/464 |
| 5,705,813 A | 1/1998 | Apffel et al. ............... 250/288 |
| 5,770,272 A | 6/1998 | Biemann et al. ........... 427/421 |

(Continued)

FOREIGN PATENT DOCUMENTS

CA    2 398 680    8/2002

(Continued)

OTHER PUBLICATIONS

Nelson, Randall W. (1996) "The Use of Bioreactive Probes in Protein Characterization", Mass Spectrometry Reviews 1997: 16, 353-376.

(Continued)

*Primary Examiner*—Nikita Wells
(74) *Attorney, Agent, or Firm*—Edwards Angell Palmer & Dodge, LLP; Peter C. Lauro, Esq.

(57) ABSTRACT

A novel Matrix-Assisted Laser Desorption/Ionization Mass Spectrometry (MALDI-MS) desalting sample support plate is described. The plate comprises a sample presentation surface, wherein the sample presentation surface comprises at least one receiving surface of an absorbent layer, wherein the absorbent layer retains selected molecules on the receiving surface. Methods for making and using the sample support plate in conventional and automated MALDI-MS are also described.

48 Claims, 4 Drawing Sheets

U.S. PATENT DOCUMENTS

| | | | |
|---|---|---|---|
| 5,770,860 A | 6/1998 | Franzen | 250/288 |
| 5,828,063 A | 10/1998 | Köster et al. | 250/288 |
| 5,859,431 A | 1/1999 | Cotrell | 250/288 |
| 5,894,063 A * | 4/1999 | Hutchens et al. | 436/155 |
| 6,004,770 A | 12/1999 | Nelson | 435/23 |
| 6,020,208 A | 2/2000 | Hutchens | 436/174 |
| 6,104,028 A | 8/2000 | Hunter et al. | 250/288 |
| 6,124,137 A * | 9/2000 | Hutchens et al. | 436/155 |
| 6,225,047 B1 | 5/2001 | Hutchens et al. | 435/5 |
| 6,265,715 B1 | 7/2001 | Perreault et al. | 250/288 |
| 6,287,872 B1 | 9/2001 | Schürenberg | 436/181 |
| 6,326,616 B1 | 12/2001 | Andrien, Jr. et al. | 250/288 |
| 6,376,044 B1 | 4/2002 | Jarrell et al. | |
| 6,555,813 B1 | 4/2003 | Beecher et al. | 250/281 |
| 6,580,070 B1 | 6/2003 | Cornish et al. | 250/287 |
| 2002/0011563 A1 | 1/2002 | Griffey et al. | 250/288 |
| 2002/0051738 A1 | 5/2002 | Schurenberg | 422/102 |
| 2002/0068133 A1 | 6/2002 | Jarrell et al. | 427/596 |
| 2002/0121595 A1 | 9/2002 | Sunner et al. | 250/281 |
| 2002/0150903 A1 | 10/2002 | Koster | 435/6 |
| 2003/0010908 A1 | 1/2003 | Clark et al. | |
| 2003/0057368 A1 | 3/2003 | Franzen et al. | 250/281 |

FOREIGN PATENT DOCUMENTS

| | | |
|---|---|---|
| DE | 196 18 032 A1 | 11/1997 |
| DE | 100 43 042 A1 | 3/2002 |
| EP | 1 274 116 A2 | 1/2003 |
| EP | 1 284 495 A2 | 8/2003 |
| GB | 2 332 273 A | 6/1916 |
| GB | 2 312 782 A | 11/1997 |
| GB | 0120131.8 | 8/2001 |
| GB | 2 369 721 A | 6/2002 |
| GB | 02 193 09 | 9/2002 |
| JP | 2001-13110 | 1/2001 |
| WO | WO 93/00700 | 1/1993 |
| WO | WO 99/16103 | 4/1999 |
| WO | WO 00/66265 | 11/2000 |
| WO | WO 00/67293 | 11/2000 |
| WO | WO 00/77812 A2 | 12/2000 |
| WO | WO 01/19520 A1 | 3/2001 |
| WO | WO 02/093170 A1 | 11/2002 |
| WO | WO 02/097392 A2 | 12/2002 |

OTHER PUBLICATIONS

Mock, K.K., et al., (1992) "Sample Immobilization Protocols for Matrix-assisted Laser-desorption Mass Spectrometry", Rapid Communications in Mass Spectrometry, vol. 6, 233-238 (1992).

Miliotis, Tasso, et al., (2001) "Ready-made matrix-assisted laser desorption/ionization target plates coated with thin matrix layer for automated sample deposition in high-density array format", Rapid communications in Mass Spectrometry, 2002; 16: 117-126.

Laiko, Victor V., et al., (2002) "Atmospheric pressure laser desorption/ionization on porous silicon", Rapid Communications in Mass Spectrometry, 2002; 16: 1737-1742.

Neubert, Hendrik, et al., (2002) "Enhanced Affinity Capture MALDI-TOF MS: Orientation of an Immunoglobulin G Using Recombinanct Protein G", Analytical Chemistry, vol. 74, No. 15, Aug. 1, 2002.

Gobom, Johan, et al., (2001) "α-Cyano-4-hydroxycinnamic Acid Affinity Sample Preparation. A Protocol for MALDI-MS Peptide Analysis in Proteomics", Analytical Chemistry, vol. 73, No. 3, Feb. 1, 2001.

Ekström, Simon, et al., (2001) "Signal Amplification Using "Spot-on-a-chip" Technology for the Identification of Proteins via MALDI-TOF MS", Analytical Chemistry, vol. 73, No. 2, Jan. 15, 2001.

Brockman, Adam H., et al., (1998), "Optimization of a Hydrophobic Solid-phase Extraction Interface for Matrix-Assisted Laser Desorption/Ionization", Journal of Mass Spectrometry, 33, 1141-1147 (1998).

Hutchens, T. Williams, et al., (1995), "Surface-Enhanced Laser Desorption/Ionization (SELDI): Probe Surfaces Enhanced for Affinity Capture (SEAC) of Energy Absorbing Molecules (EAM) for Neat Desorption (SEND) of Intact Biopolymers", Microbeam Anal. Proc. Annu. Conf., Microbeam Anal. Soc. 29$^{th}$ (1995) pp. 41-42.

Zhang, Li, et al., (1999), "Solid-Phase Extraction/MALDI-MS: Extended Ion-Pairing Surfaces for the On-Target Cleanup of Protein Samples", Analytical Chemistry, vol. 71, No. 20, Oct. 15, 1999.

McComb, Mark E., et al., (1997), "Use of a Non-porous Polyurethane Membrane as a Sample Support for Matrix-assisted Laser Desorption/Ionization Time-of-flight Mass Spectrometry of Peptides and Proteins", Rapid Communication in Mass Spectrometry, vol. 11, 1716-1722 (1997).

Smirnov, Igor P., et al., (2001), "Application of DNA-binding polymers for preparation of DNA for analysis by matrix-assisted laser desorption/ionization mass spectrometry", Rapid Communications in Mass Spectrometry, 2001; 15: 1427-1432.

Brockman, Adam H., et al., (1997), "A Desalting Approach for MALDI-MS Using On-Probe Hydrophobic Self-Assembled Monolayers", Analytical Chemistry, vol. 69, No. 22, Nov. 15, 1997.

Brockman, Adam H., et al., (1996), "New Immobilization Chemistry for Probe Affinity Mass Spectrometry", Rapid Communications in Mass Spectrometry, vol. 10, 1688-1692 (1996).

Warren, Maria Esteban, et al., "On-Probe Solid-Phase Extraction/MALDI-MS Using Ion-Pairing Interactions for the Cleanup of Peptides and Proteins", Analytical Chemistry, vol. 70, No. 18, Sep. 15, 1998.

Hutchens, William T., et al., (1993), "New Desorption Strategies for the Mass Spectrometric Analysis of Macromolecules", Rapid Communications in Mass Spectrometry, vol. 7, 576-580 (1993).

Ching, Jesus, et al., (1996), "Surface Chemistries Enabling Photoinduced Uncoupling/Desorption of Covalently Tethered Biomolecules", Americal Chemical Society, (1996), 61, 3582-3583.

Merchant, Maggie, et al., (2000), "Recent Advancements in Surface-Enhanced Laser Desorption/Ionization-time of Flight-mass Spectrometry", Electrophoresis 2000, 21, 1164-1167.

Gilar, Martin, et al., "Advances in Sample Preparation in Electromigration, Chromatographic and Mass Spectrometric Separation Methods", Journal of Chromatography A, 909 (2001) 111-135.

Nelson, Randall W., "The Use of Bioreactive Probes in Protein Characterization", Mass Spectrometry Reviews, Apr. 30, 1996, vol. 16, pp. 353-376, 1998 by John Wiley & Sons, Inc., USA

* cited by examiner

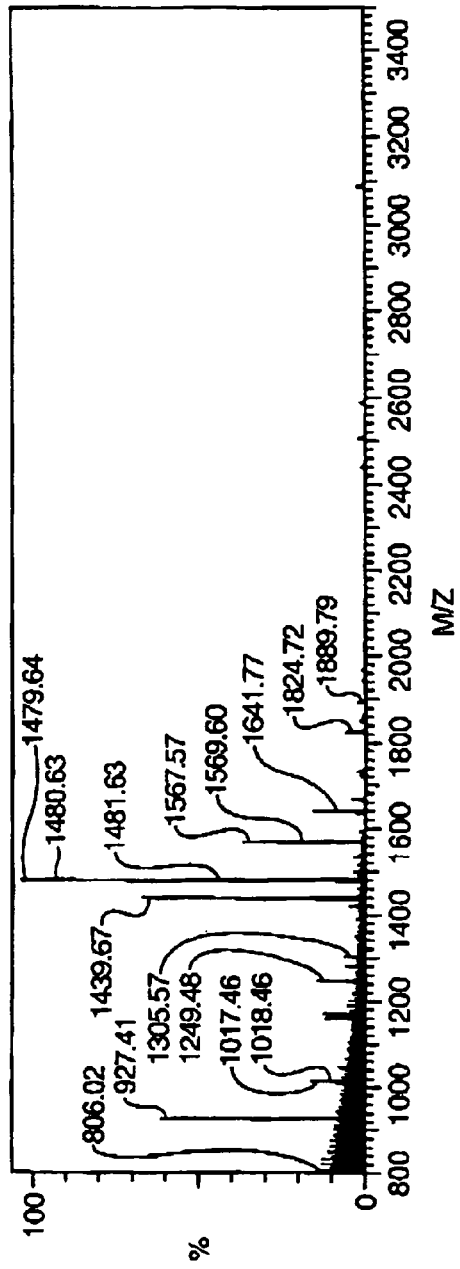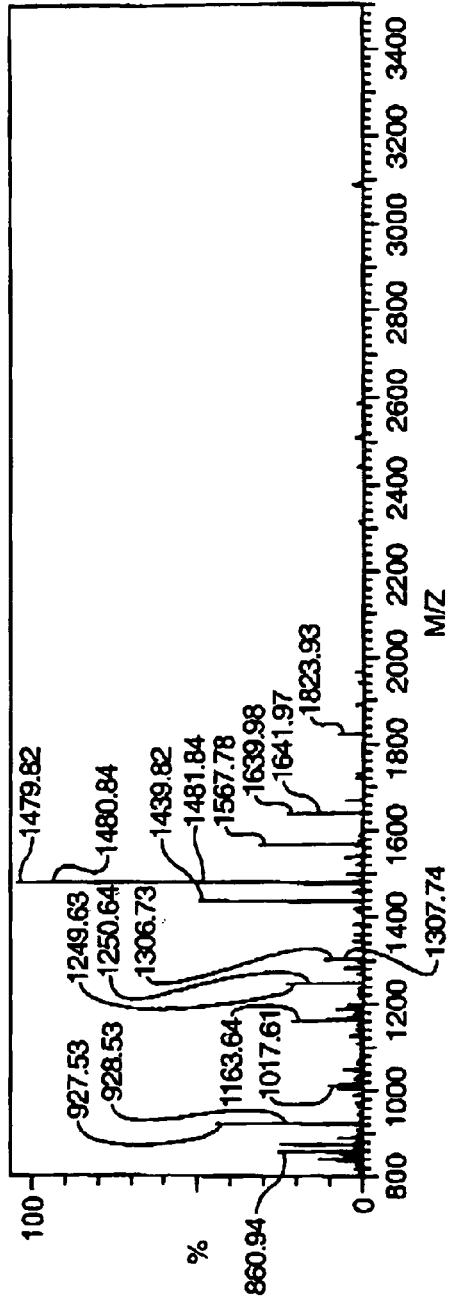
FIG. 4A
FIG. 4B

DESALTING PLATE FOR MALDI MASS SPECTROMETRY

This application is a U.S. national phase application, pursuant to 35 U.S.C. §371, of PCT international application Ser. No. PCT/US02/16501 filed May 24, 2002, designating the United States, and published in English as international publication WO 02/096541 A1 on Dec. 5, 2002, which claims priority to U.S. provisional application Ser. No. 60/293,496 filed on May 25, 2001. The entire contents of the aforementioned patent applications are incorporated herein by this reference.

BACKGROUND OF THE INVENTION

Mass spectrometry (MS) with ionization by matrix-assisted laser desorption and ionization (MALDI) has become a useful tool for the analysis of large molecules, e.g., biopolymers, such as proteins, peptides, oligonucleotides, DNA, RNA, etc. It is well known that the sensitivity of the analysis and the speed of automation are highly dependent on preparation and purity of the sample on the MALDI plate. Many of the issues associated with sample preparation for MALDI mass spectrometry are summarized in Bruker's UK patent application (GB 2332273A). In particular, salts can dramatically affect the quality of the resulting mass spectra due to adduct formation.

One existing method for salt removal utilizes reversed-phase sorbents such as C18-silica or divinylbenzene-based polymers. For example, a mixture of analytes is passed through a packed bed containing such sorbents, and the analytes adsorb to the packing material, while the salts are not retained. The adsorbed analytes are subsequently eluted from the sorbent with an appropriate solvent. Several commercially available products are available for this application.

However, all of these products require several manipulation steps prior to application of the sample onto the MALDI plate. These additional steps may lead to significant sample loss and potential re-contamination of the sample. In addition, samples typically become diluted during the sample preparation step because of the relatively large elution volumes that are required. Because the MALDI laser focuses on only a small percentage of the total area of the applied sample, only a small fraction of the applied diluted sample will be vaporized and detected, resulting in decreased sensitivity.

An additional problem with spotting a sample onto a traditional MALDI plate pertains to the drying of the sample on the plate. As the sample dries, the target analyte randomly concentrates in localized regions. As a result, analysis time for each sample increases, as the laser may need to search until it finds the target analyte that is sufficient for analysis. For example, when a drop of sample and matrix solution that is placed onto a clean metal sample support plate dries on a metal surface, the sample spot consisting of small matrix crystals spreads over the formerly wet area. In general, the wetted area is not uniformly coated. In aqueous solutions, most of the small crystals of the matrix generally begin to grow at the margin of the wet area on the metal plate and continue to grow toward the center of the wet area. Thus the analyte molecules are irregularly distributed, and the center of the spot is frequently empty or covered with fine small crystals. These crystals are not typically sufficient for MALDI ionization due to the high concentration of salts. Furthermore, the MALDI ionization yield and mass resolution fluctuate in the sample spot from site to site. It is often a troublesome process to find a favorable location on the sample spot with good analyte ion yield and good mass resolution. Consequently, the development of high sample throughput automation of MALDI mass spectrometry analysis has been hindered.

British patent application GB 2332273A describes a MALDI plate, coated with a Teflon-like hydrophobic coating having hydrophilic patches ("anchors"), which utilizes surface property (hydrophilic or hydrophobic) modification on the plate. After sample droplets are deposited onto the anchors, the droplets shrink during solvent evaporation, thereby centering themselves onto the anchor positions. Thus, MS detection sensitivity increases 10 to 100 times as compared to the conventional dried sample droplet preparation method described above, because the analyte is concentrated in smaller spots. The sample spots can be arranged in a precise grid to facilitate rapid, automated MALDI-MS. Such coated plates (AnchorChip™) are marketed by Bruker Daltonics®. However, these plates are incapable of retaining analyte molecules during a wash step, used to remove salts that may interfere with the analysis of the analyte.

U.S. Pat. Nos. 6,020,208 and 6,124,137 describe a MALDI-MS plate design in which the presentation surface of the target spot is derivitized with affinity molecules which allow for specific or nonspecific capturing of analytes of interest on the presentation surface. The sensitivity as well as the efficiency of the analysis by MALDI-MS are reportedly improved over conventional methods. The molecules that are not used for analysis may be subjected to further processing and subsequently further analysis on the presentation surface.

Published PCT applications WO 98/59360, WO 98/59361, WO 98/59362, and their corresponding European patent applications, EP 00990256, EP 00990257, and EP 00990258 describe plates, and methods of retentate chromatography for retaining selected molecules on a variety of adsorbents and using a variety of selectivity conditions. Upon selection of the highest affinity conditions direct MALDI-MS is used to analyze the selected molecule.

U.S. Pat. No. 5,480,526 describes the removal of salts from samples analyzed by MALDI-MS by using capillary electrophoresis methods prior to the analysis.

U.S. Pat. No. 6,104,028 describes the improvement of the sensitivity and resolution of MALDI-MS by improvement of the matrices.

U.S. Pat. Nos. 5,260,571, 5,281,538, and 5,308,978 describe improvement in sensitivity and resolution of detection by applying the matrix as a layer to the target spot of the MALDI-MS sample plate prior to the application of the sample, to thereby provide, after drying, an intimate mixture of sample and matrix material. Similarly, U.S. Pat. No. 5,595,636 describes the use of a thin lacquer-like smooth matrix layer applied prior to the application of the sample to assist in the desorption of the analyte molecules.

U.S. Pat. Nos. 5,770,860, 5,770,272, and 5,705,813 describe improved devices for use in connection with mass spectrometric analysis. In particular, U.S. Pat. No. 5,770,272 describes a nebulizing sprayer that deposits a continuous, homogeneous layer of MALDI matrix material on MALDI targets. U.S. Pat. No. 5,705,813 describes an integrated liquid handling system for manipulation of a sample prior to mass analysis by MALDI-MS. U.S. Pat. No. 5,770,860 discloses a method for loading sample supports of a mass spectrometer using a multiple pipette unit to simultaneously transfer multiple samples from microtiter plates. Repeated loading, in this fashion, generates high-density samples on the sample plate.

Nevertheless, a need exists for technological advancement of the MALDI-MS sample design that is capable of desalting samples directly on the MALDI plate while retaining the analyte and matrix on an underivatized surface, such that the salts may be washed away by the use of an appropriate solvent, e.g., water, and thereby reduce the number of sample manipulation steps while improving the sensitivity and resolution of detection by MALDI-MS by MALDI-MS. The use of small spots of the sample would localize the sample into a specific area, removing the requirement of searching for the sample location.

SUMMARY OF THE INVENTION

The invention is directed to a desalting sample support plate for MALDI-MS. The invention provides convenient methods of preparation and use of the support plate. Additionally, the invention provides methods of sample preparation and analysis. Furthermore, the methods of sample preparation and analysis of the present invention are capable of desalting samples directly on the MALDI plate while retaining the analyte and matrix on an underivatized surface, such that the salts may be washed away by the use of an appropriate solvent, e.g., water, and thereby reduce the number of sample manipulation steps while improving the sensitivity and resolution of detection by MALDI-MS. The use of small spots of the sample localizes the sample into a specific area, thereby obviating the need to search for the sample location.

Thus, in one aspect, the invention is a desalting sample support plate for use in Matrix-Assisted Laser Desorption/Ionization Mass Spectrometry (MALDI-MS). The MALDI plate comprises a sample presentation surface, wherein the sample presentation surface comprises at least one receiving surface of an adsorbent layer. The adsorbent layer retains selected molecules on the receiving surface.

Another aspect of the invention is a method for preparing a sample for MALDI-MS. Providing the sample support plate described above, a sample is applied to the receiving surface. Selected molecules in the sample are retained on the adsorbent layer. A solvent is applied to the receiving surface to wash away salts and other impurities, thus desalting the sample applied to the target spot, to thereby prepare a sample for MALDI-MS.

In yet another aspect, the invention is a method for preparing the sample support plate described above. A sample support plate is provided, comprising a sample presentation surface, and at least one receiving surface of an adsorbent layer. The adsorbent layer retains selected molecules on the receiving surface.

In a related aspect, the invention is a method for preparing the sample support plate as described above. The method comprises forming, on a sample support plate having a sample presentation surface, at least one receiving surface of an adsorbent layer. The adsorbent layer retains selected molecules on the receiving surface.

Another aspect of the invention is a method for performing Matrix-Assisted Laser Desorption/Ionization Mass Spectrometry (MALDI-MS) on an analyte of interest using the desalting plate described above. The method comprises providing a sample support plate comprising a sample presentation surface, wherein the sample presentation surface comprises at least one receiving surface of an adsorbent layer, wherein the adsorbent layer retains selected molecules on the receiving surface; applying a sample comprising an analyte of interest to the receiving surface of the adsorbent layer; allowing the analyte of interest in the sample to be retained on the adsorbent layer; washing the adsorbent layer with an aqueous solution to remove the salts from the adsorbent layer, thereby desalting the sample; and performing MALDI-MS on the desalted analyte of interest retained on the adsorbent layer.

BRIEF DESCRIPTION OF THE DRAWINGS

FIG. 4 illustrates the comparison analysis by MALDI-MS of small and large diameter polymer coatings on a sample plate that has been washed, as above, following the application of a BSA tryptic digest.

DETAILED DESCRIPTION OF THE INVENTION

Figure 1A:
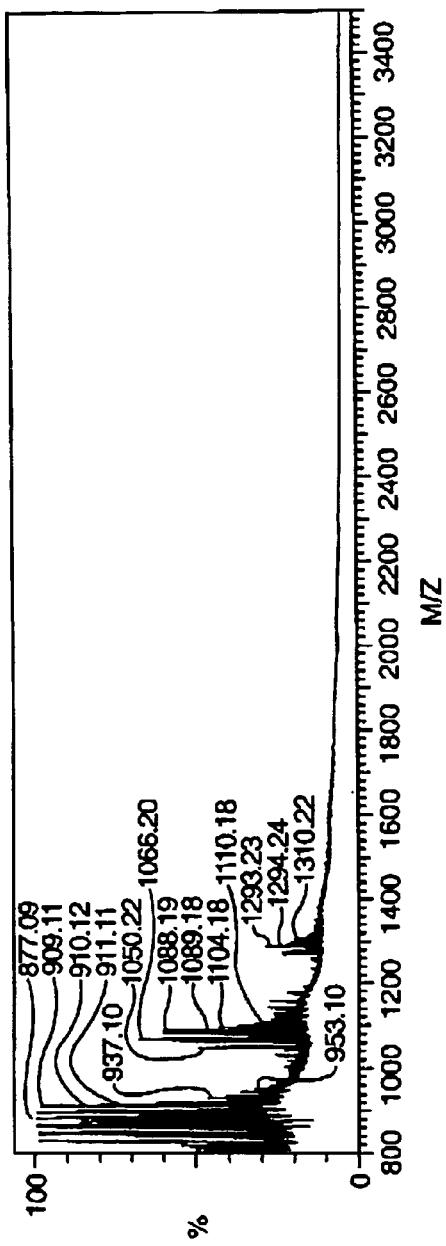
FIG. 1 illustrates the comparison analysis by MALDI-MS of a blank sample plate with and without a polymer coating according to the invention.

The invention is directed to a desalting sample support plate for MALDI-MS. The invention provides convenient methods of preparation and use of the support plate. Additionally, the invention provides methods of sample preparation and analysis. Furthermore, the methods of sample preparation and analysis of the present invention are capable of desalting samples directly on the MALDI plate while retaining the analyte and matrix on an underivatized surface, such that the salts may be washed away by the use of an appropriate solvent, e.g., water, and thereby reduce the number of sample manipulation steps while improving the sensitivity and resolution of detection by MALDI-MS. The use of small spots of the sample serves to localize the sample into specific areas, thereby obviating the need to search for the sample location.

Definitions

Before further description of the invention, certain terms employed in the specification, examples, and appended claims are, for convenience, collected here.

The terms "sample support plate" or "sample plate" as used herein refer to an apparatus on which a sample is placed for analysis by MALDI-MS. Conventional MALDI-MS sample support plates can be coated with a sufficiently adsorbent material, forming an adsorbent layer on a receiving surface, e.g., on a target spot, in order to prepare the support plates of the invention.

The term "target spot" as used herein refers to the designated area of the sample support plate for the analysis of one particular sample or a mixture of samples.

The terms "adsorbent layer" or "sufficiently adsorbent" as used herein refer to any material, e.g., a polymeric film or coating, that is capable of retaining selected molecules, e.g., the analyte of interest, without having been derivatized or chemically modified. The adsorbent layer may preferentially adsorb selected molecules, e.g., the analyte of interest, from other molecules, e.g., salts; this enables the removal of unwanted species from the adsorbant layer by appropriate choice of washing protocols. The adsorbent layer may be substantially nonporous such that molecules applied to the adsorbent layer are not absorbed or do not penetrate the layer. Alternatively, sufficiently porous adsorbent layers of the invention can be used to increase surface area, thereby increasing the concentration of the retained selected molecules and enhancing sensitivity of the analysis.

The term "salts" as used herein refers to any molecule, including alkali salts, that adversely affects the quality of the mass spectrum of an analyte of interest because of adduct formation.

The term "analyte of interest" as used herein refers to the molecule or molecules that are to be analyzed.

The term "matrix material" as used herein refers to any material suitable for use in MALDI-MS, and includes one or more of several small, acidic, light absorbing chemicals, e.g., nicotinic or sinapinic acid, that is mixed in solution with the analyte in such a manner so that upon drying on the target spot, the crystalline matrix-embedded analyte molecules are successfully desorbed (by laser irradiation) and ionized from the solid phase crystals into the gaseous or vapor phase and accelerated as molecular ions. A large fold excess of the matrix material facilitates crystal formation and entrapment of analyte.

The term "selected molecules" as used herein refers to the molecules that are retained for the purpose of analysis, e.g., an analyte of interest, a matrix material, or a combination of an analyte of interest and a matrix material. Selected molecules are distinct from other molecules, such as salts, which are removed by the methods of the invention for the purpose of improving analysis by MALDI-MS.

The terms "aqueous solution" or "aqueous solvent" as used herein refer to water and liquids that have water as a component. This term is meant to include solutions that contain additional components, such as organic or inorganic compounds dissolved in the solution, and organic or inorganic solvents that are miscible with water. For example, a mixture of water and methanol is considered an aqueous solution.

The term "receiving surface" as used herein refers to an area of the presentation surface to which the adsorbent layer is applied. The adsorbent layer is applied to the receiving surface without any modification, e.g., conditioning by physical or chemical modification.

The term "selection criterion" as used herein refers to a property (e.g., hydrophobicity) by which the adsorption layer achieves reverse phase separation of molecules applied to the layer.

Description of Certain Embodiments of the Invention

In one aspect, invention is a desalting sample support plate for use in Matrix-Assisted Laser Desorption/Ionization Mass Spectrometry (MALDI-MS). The MALDI plate comprises a sample presentation surface, wherein the sample presentation surface comprises at least one receiving surface of an adsorbent layer. The adsorbent layer retains selected molecules on the receiving surface. The invention is also directed to methods of sample support plate preparation, sample preparation, and analysis.

The adsorbent layer is sufficiently adsorbent to allow retention of selected molecules on the adsorbent layer. In certain other embodiments of the invention the selected molecules that are retained on the surface of the adsorbent layer are selected from an analyte, a matrix, and combinations thereof. In a preferred embodiment, the adsorbent layer is a polymeric film.

In one embodiment of the invention, the target-spot comprises a receiving surface in a precisely defined location that facilitates automated analysis. In another embodiment, the MALDI-MS sample plate of the invention comprises a plurality of receiving surfaces and associated receiving surfaces, such that a grid of receiving surfaces is formed on the sample presentation surface. The plurality of receiving surfaces facilitates high throughput analysis. In a preferred embodiment, the grid comprises 96 receiving surfaces.

Another aspect of the invention is a method for preparing the MALDI-MS sample support plate described above. A sample support plate having a sample presentation surface is provided. Just about any material can be used to make the sample support plate, but the material used should not deleteriously react with the reagents used for preparation of the sample, and also should be able to withstand the conditions typically used during MALDI-MS. Suitable materials include plastics (for example, polyolefins, especially polyethylene and polypropylene, PVC and polystyrene), glass and metal (for example, stainless steel). In preferred embodiments, the material used to make the sample support plate is electrically conductive.

In certain embodiments, the presentation surface is formed with at least one receiving surface of an adsorbent layer. The receiving surface of the adsorbent layer is created by applying a solution of the adsorbent layer onto the sample presentation surface of the plate. In one embodiment, the adsorbent layer is "spotted" onto the surface using a pipettor. In other embodiments, spotting is performed by solenoid actuated valves or by piezoelectric deposition. In another embodiment, the spotting is performed with a pin, using a technique known to those skilled in the art.

In preferred embodiments, the adsorbent material facilitates reverse phase separation of molecules in the sample. Thus, selected molecules, e.g., the analyte of interest, are retained by nonspecific binding to the layer, while other molecules, e.g. salts, are not retained and can be washed away. For example, the adsorbent layer can be hydrophobic and wettable, e.g., by water, at the same time.

In preferred embodiments, the adsorbent layer comprises a polymeric film. The polymeric film is prepared by admixing a monomer, a polymer, or a combination thereof, a porogen, and an initiator. Alternatively, in other embodiments, the polymeric film is prepared by admixing a monomer, a polymer, or a combination thereof, and an initiator. In a particular embodiment, the polymer is selected from polystyrene and polyvinylpyrrolidinone.

In certain embodiments, the monomer is a monovinyl monomer, a polyvinyl monomer, or a mixture of monovinyl and polyvinyl monomers. Monovinyl monomers that can be used include, for example, styrene, N-vinylpyrrolidinone, methacrylate, vinylacetate, glycidyl methacrylate, and any combination thereof. In one embodiment, the monovinyl monomer is N-vinylpyrrolidinone.

Polyvinyl monomers that can be used include, for example, divinylbenzene, ethylene dimethacrylate, bis-acrylamide, divinylpyridine, ethylene dimethacrylate, hydroxyalkylene dimethacrylate, or any combination thereof. In one embodiment, the polyvinyl monomer is divinylbenzene. In another embodiment, the mixture of monovinyl monomer and polyvinyl monomer is divinylbenzene and N-vinylpyrrolidinone.

Suitable porogens include, for example, aliphatic hydrocarbons, aromatic hydrocarbons, esters, alcohols, ketones, ether, or any combination thereof. Likewise, suitable initiators include, for example, benzoyl peroxide, lauroyl peroxide, peroxodisulfate, Vazo 52, Vazo 64, Vazo 67, Vazo 88, V70, or any combination thereof In a specific embodiment of the invention, the sample support plate of the invention is prepared by admixing a monomer, a polymer, or a combination thereof, a porogen, and an initiator; coating, e.g., by pipetting, a receiving surface on the support plate with the admixture; initiating a polymerization reaction to form a polymeric film; and washing the polymeric film to remove residual monomer, porogen and initiator. Alternatively, the method is carried out as just described, except that a porogen is not used.

In certain embodiments, the coated sample support plate is treated, prior to application of the sample, with organic solvents, in particular polar organic solvents. Exemplary polar organic solvents include acetonitrile, methanol, or water/organic solvent mixtures.

Another aspect of the invention is a method for preparing a sample for MALDI-MS. A sample support plate of the invention as described above is provided, and a sample is applied to the receiving surface on the target spot. Selected molecules in the sample are retained on the adsorbent layer. Thus, the sample applied to the receiving surface at the target spot is effectively desalted. In certain embodiments, the adsorbent layer is washed with an aqueous solution to remove the salts from the adsorbent layer.

As noted above, in certain embodiments, the coated sample support plate is treated, prior to application of the sample, with organic solvents, in particular polar organic solvents. Polymeric materials that possess relatively low surface area, e.g., due to low monovinyl monomer incorporation into the polymeric film may require pretreatment with organic solvents. Such treatment provides sufficient wetting of the surface of the adsorbent layer, thereby enhancing retention of the selected molecules at the surface of the adsorbent layers.

In certain embodiments, the sample comprises an analyte of interest, a matrix material, one or more salts, and one or more solvents. In specific embodiments, the solvent is aqueous. In certain embodiments, the sample contains a solution of a matrix material. In other embodiments, the sample does not contain a matrix material. In yet other embodiment, the matrix material is added after the adsorbent layer is washed with an aqueous solution.

Another aspect of the invention is a method for performing Matrix-Assisted Laser Desorption/Ionization Mass Spectrometry (MALDI-MS) on an analyte of interest using the sample support plate of the invention as described above. The method comprises: providing the sample support plate described above, applying a sample comprising an analyte of interest to the receiving surface of the adsorbent layer; allowing the analyte of interest in the sample to be retained on the adsorbent layer; washing the adsorbent layer with an aqueous solution to remove the salts from the adsorbent layer, thereby desalting the sample; and performing MALDI-MS on the desalted analyte of interest retained on the adsorbent layer.

In certain embodiments of the invention the presentation surface comprises at least one sample target spot, wherein the target spot comprises the adsorbent layer.

Exemplification of the Invention

The invention is further illustrated by the following examples that should not be construed as limiting.

EXAMPLE 1

Preparation of Polymer Spotted Plates and Initial Evaluation

A monomer solution of 9.75 g of divinylbenzene, 5.25 g of N-vinylpyrrolidinone, and 0.3 g of V70 (initiator) was prepared. Using a pipettor, the monomer solution was spotted onto the receiving surface of a conventional, steel MALDI plate. The resulting plate contained rows of spots that were heavily coated with the monomer solution (labeled Rows A–D), as well as rows of spots having a very small amount of monomer solution (labeled Rows E–H). The plate was heated overnight in oven at about 60° C. to initiate polymerization and form a non-porous polymeric coating at each of the spots on the plate.

The plate contained non-porous films spotted over the target spots of the MALDI-MS plates. The plate was briefly washed by sonication in methanol, followed by sonication in methylene chloride. The plate was then prepared for analysis using the following methodology.

1. Conditioning of polymer coating
   Washed polymer coating with 1 μL 100% acetonitrile
   Washed polymer coating with 1 μL 80% acetonitrile
   Removed acetonitrile and wash with 2 μL 0.1% trifluoroacetic acid
2. Binding of the sample
   Removed 0.1% trifluoroacetic acid
   Loaded 2 μL sample in 0.1% trifluoroacetic acid
   Allowed solvent to evaporate to dryness
3. Washing of the sample
   Added 2 μL 0.1% trifluoroacetic acid on target
   Incubated for 4 mins
   Removed Wash solution
   Repeated
4. Addition of the matrix material
   Added 0.5 μL α-cyano (5 mg/mL:25% acetonitrile, 25% EtOH, 0.05% trifluoroacetic acid)
   Evaporated to dryness The plate, as prepared above, was compared to a conventional MALDI-MS plate without the presence of a sample, to determine the presence of background contaminants. The sample, a bovine serum albumin (BSA) tryptic digest, was then analyzed in comparison to a control sample that was prepared without a polymer coating by MALDI-MS to determine the ionization ability of a peptide on the coated receiving surface. The polymer coated MALDI-MS plate containing the tryptic digest sample was then washed two times with water and the results were compared with the results of the unwashed sample. A polymer coated MALDI-MS was prepared, as described above, with a relatively larger diameter of the polymer coating and the results were compared.

Figure 1B:
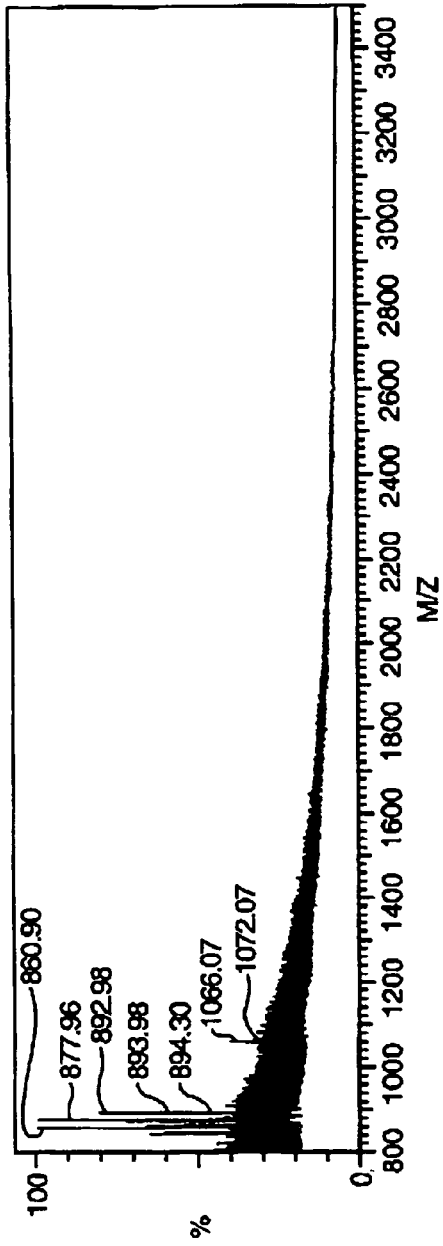
Figure 2A:
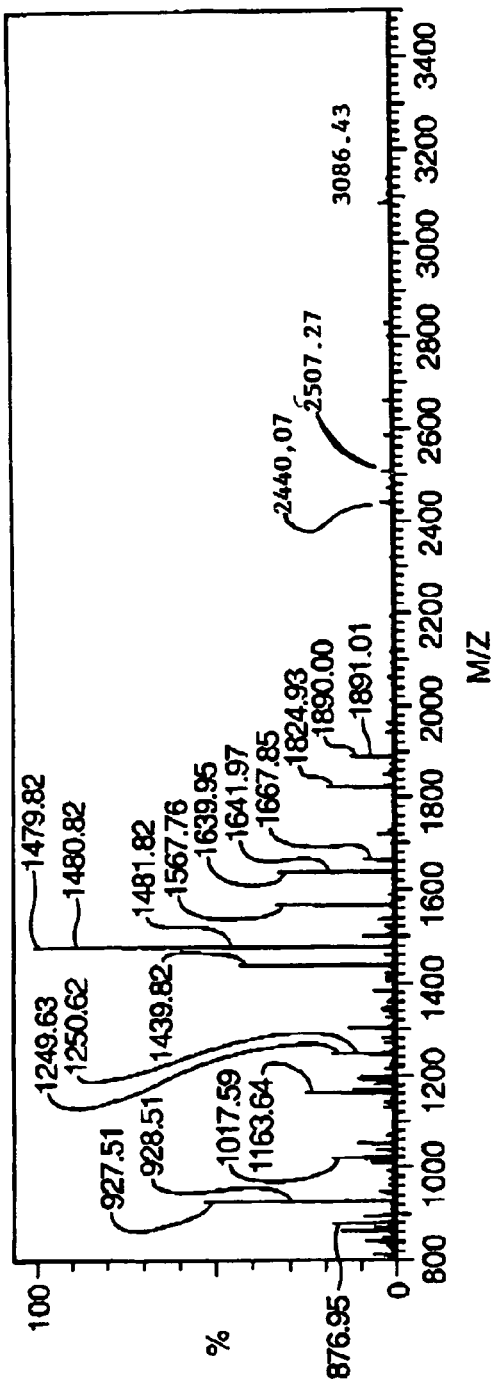
FIG. 2 illustrates the comparison analysis by MALDI-MS of a Bovine Serum Albumin (BSA) tryptic digest on a sample plate with and without a polymer coating.
Figure 2B:
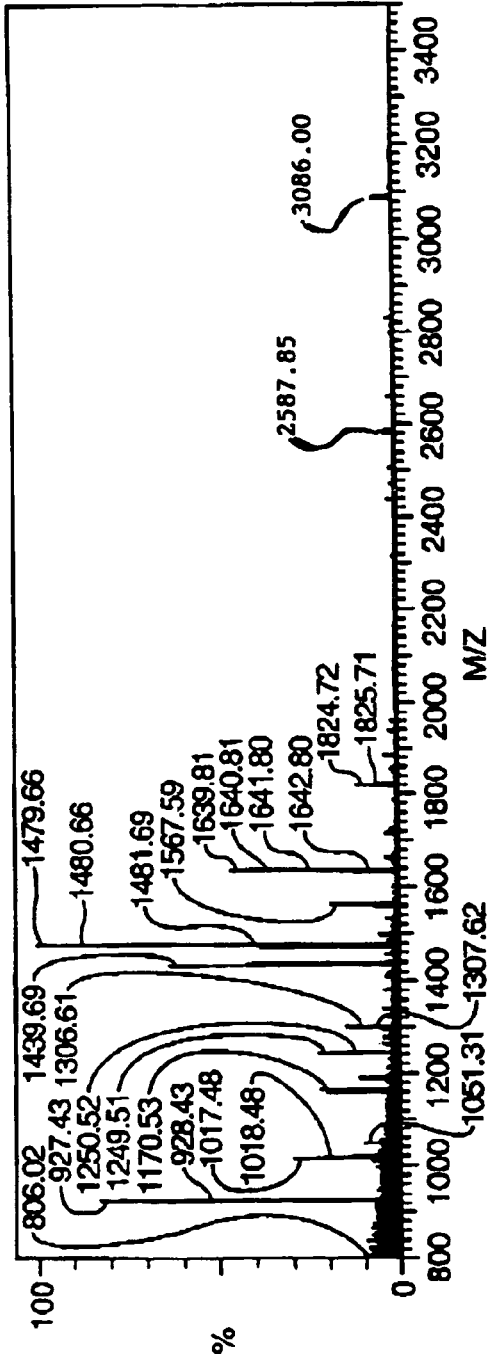
Figure 3A:
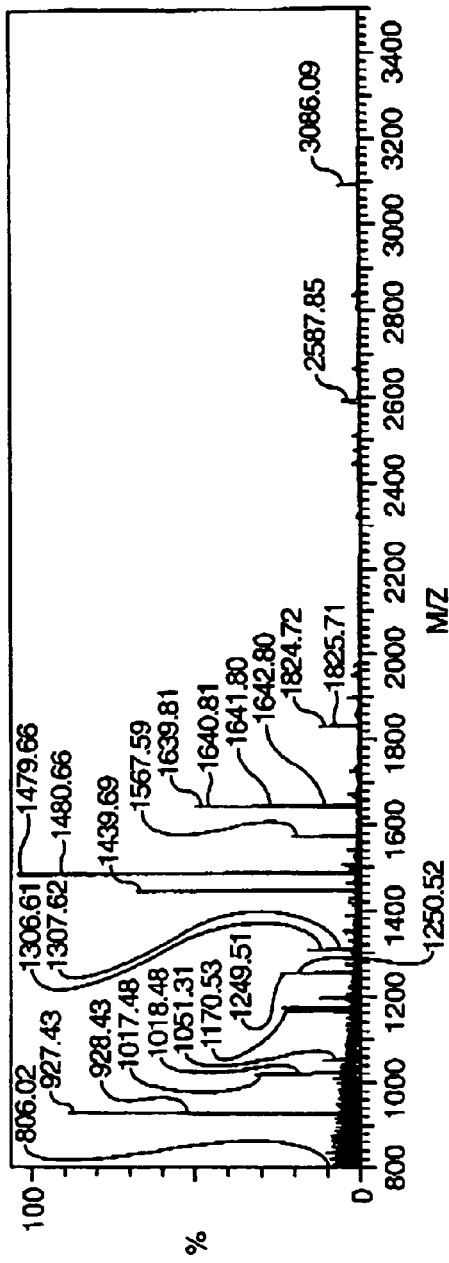
FIG. 3 illustrates the comparison analysis by MALDI-MS of the sample plate before and after washing the polymer-coated plate, described in FIG. 2, two times with water.
Figure 3B:
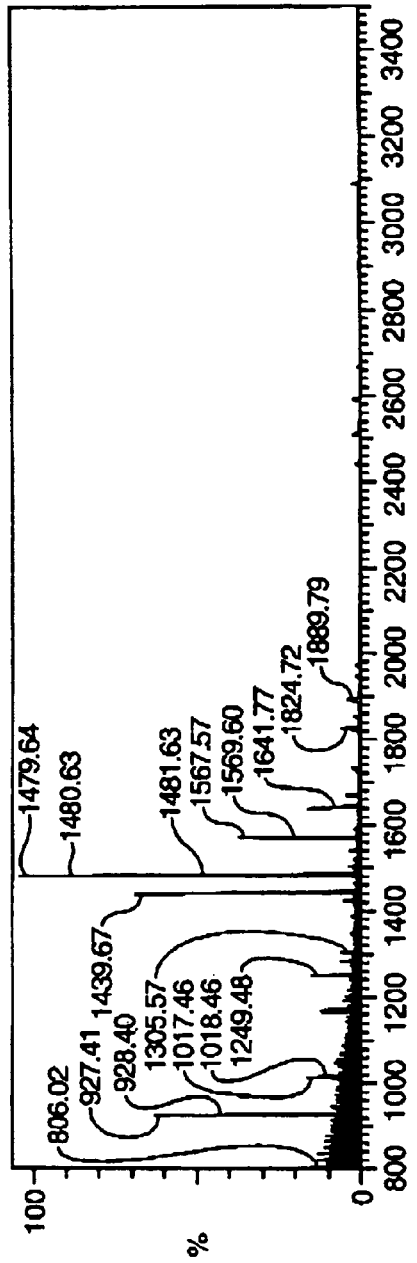

FIGS. 1 through 4 illustrate the results of the above comparative analyses as follows:

1. The polymer coating does not produce a significant background in MALDI TOF-MS.
2. The BSA did ionize from the polymer coating.
3. The BSA did bind to the coating and was capable of undergoing a washing step.
4. The signal to noise ratio may be improved with a smaller diameter coating.

EXAMPLE 2

Preparation of Several Coating Compositions on a MALDI-MS Plate

Several coating compositions were prepared using polystyrene (mw, 280,000; Aldrich 18242-7, lot 130 15902 CI), polyvinylpyrrolidinone (mw, 360,000; Sigma P-5288, lot 38H0092), and 1-methyl-2-pyrrolidinone (Aldrich 44377-8, lot PI 00850 MI) and were spotted on a MALDI-MS plate in the following manner.

1.) Spots A1 to A12 were spotted with a polymer solution that was a mixture of 1 gram of polystyrene and 15 ml of 1-methyl-2-pyrrolidinone in a 20 ml glass vial
2.) Spots B1 to B12 were spotted with a polymer solution that was a mixture of 0.9 gram of polystyrene, 0.1 gram of polyvinylpyrrolidinone and 15 ml of 1-methyl-2-pyrrolidinone in a 20 ml glass vial.
3.) Spots C1 to C12 were spotted with a polymer solution that was a mixture of 0.8 gram of polystyrene, 0.2 gram of polyvinylpyrrolidinone and 15 ml of 1-methyl-2-pyrrolidinone in a 20 ml glass vial.
4.) Spots D1 to D12 were spotted with a polymer solution that was a mixture of 0.7 gram of polystyrene, 0.3 gram of polyvinylpyrrolidinone and 15 ml of 1-methyl-2-pyrrolidinone in a 20 ml glass vial.
5.) Spots E1 to E12 were spotted with a polymer solution that was a mixture of 0.6 gram of polystyrene, 0.4 gram of polyvinylpyrrolidinone and 15 ml of 1-methyl-2-pyrrolidinone in a 20 ml glass vial.
6.) Spots F1 to F12 were spotted with a polymer solution that was a mixture of 0.5 gram of polystyrene, 0.5 gram of polyvinylpyrrolidinone and 15 ml of 1-methyl-2-pyrrolidinone in a 20 ml glass vial.

The plate was placed in an oven at about 60° C. for one hour, subsequently placed in an ultrasonic bath with acetonitrile for 10 seconds, and ultimately washed with methanol.

EXAMPLE 3

A Second Approach to MALDI-MS Plate Preparation

Four MALDI-MS plates were prepared by spotting a polymer solution (mixture of polystyrene and polyvinylpyrrolidinone in 1-methyl-2-pyrrolidinone) on a steel MALDI plate followed by the removal of 1-methyl-2-pyrrolidinone by heating to form polymer film spots. This approach was designed to ease the difficulty of plate preparation associated with the nonuniformity of initiation of polymerization on the plate, and to probe the background noise and sensitivity issues. The plates were prepared by the following methods, and were designed as a comparison to the plate prepared in Example 2.
1) Polystyrene (average mw, 2,802,000) and polyvinylpyrrolidinone (average MW, 360,000) were dissolved in 1-methyl-2-pyrrolidinone.
2) The polymer solution was spotted on the MALDI plate.
3) The plate was placed in oven to remove 1-methyl-2-pyrrolidinone and form a polymer film.

The polymer solutions that were spotted on the MALDI plate were labeled polymer solution A and polymer solution B. Polymer solution A was a mixture of 1.6 gram of polystyrene (average mw, 280,000), 0.4 gram of polyvinylpyrrolidinone (average mw, 360,000), and 15 ml of 1-methyl-2-pyrrolidinone. Polymer solution B was a mixture of 1.0 gram of polystyrene (average mw, 280,000), 1.0 gram of polyvinylpyrrolidinone (average mw, 360,000), and 15 ml of 1-methyl-2-pyrrolidinone.

Two plates were spotted with about 0.05 μL of polymer solution A.

An additional two plates were spotted with about 0.05 μL of polymer solution B.

Incorporation by Reference

The entire contents of all patents, published patent applications and other references cited herein are hereby expressly incorporated herein in their entireties by reference.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A desalting sample support plate, for use in Matrix-Assisted Laser Desorption/Ionization Mass Spectrometry (MALDI-MS), comprising a sample presentation surface, wherein the sample presentation surface comprises at least one receiving surface of an adsorbent layer comprising a polymeric film, wherein when the adsorbent layer is washed with an aqueous solution to remove salts, it retains selected molecules on the receiving surface.

2. The sample plate of claim 1, wherein the adsorbent layer is sufficiently adsorbent to allow retention of selected molecules on the adsorbent layer.

3. The sample plate of claim 2, wherein the polymeric film is prepared by admixing a monomer, a polymer, or a combination thereof, a porogen, and an initiator.

4. The method of claim 3, wherein the polymer is selected from the group consisting of polystyrene and polyvinylpyrrolidinone.

5. The sample plate of claim 4, wherein the monovinyl monomer is selected from the group consisting of styrene, N-vinylpyrrolidone, methacrylate, vinylacetate, glycidyl methacrylate, and any combination thereof.

6. The method of claim 4, wherein the monovinyl monomer is N-vinylpyrrolidone.

7. The sample plate of claim 4, wherein the polyvinyl monomer is selected from the group consisting of divinylbenzene, ethylene dimethacrylate, bis-acrylamide, divinylpyridine, ethylene dimethacrylate, hydroxyalkylene dimethacrylate, and any combination thereof.

8. The MALDI-MS sample plate of claim 7, wherein the precisely defined location of the receiving surface facilitates automated analysis.

9. The method of claim 4, wherein the polyvinyl monomer is divinylbenzene.

10. The method of claim 4, wherein the mixture of monovinyl monomer and polyvinyl monomer is divinylbenzene and N-vinylpyrrolidone.

11. The sample plate of claim 3, wherein the monomer is selected from the group consisting of a monovinyl monomer, a polyvinyl monomer, and a mixture of monovinyl and polyvinyl monomers.

12. The sample plate of claim 3, wherein the porogen is selected from the group consisting of aliphatic hydrocarbons, aromatic hydrocarbons, esters, alcohols, ketones, ether, and any combination thereof.

13. The sample plate of claim 3, wherein the initiator is selected from the group consisting of benzoyl peroxide, lauroyl peroxide, peroxodisulfate, Vazo 52, Vazo 64, Vazo 67, Vazo 88, V70, and any combination thereof.

14. The sample plate of claim 2, wherein the polymeric film is prepared by admixing a monomer, a polymer, or a combination thereof, and an initiator.

15. The sample plate of claim 1, the selected molecules that are retained on the surface of the adsorbent layer are selected from the group consisting of an analyte, a matrix, and a combination thereof.

16. The MALDI-MS sample plate of claim 1, wherein the receiving surface is in a precisely defined location.

17. The MALDI-MS sample plate of claims 16, comprising a plurality of receiving surfaces, such that a grid of receiving surfaces is formed on the sample presentation surface.

18. The MALDI-MS sample plate of claim 17, wherein the grid comprises 96 receiving surfaces.

19. The MALDI-MS sample plate of claim 17, wherein the plurality of receiving surfaces facilitates high throughput analysis.

20. A method for preparing a sample for Matrix-Assisted Laser Desorption/Ionization Mass Spectrometry (MALDI-MS) comprising:
providing the sample support plate of claim 1;
applying a sample to the receiving surface;
allowing selected molecules in the sample to be retained on the adsorbent layer; and
applying a solvent to the receiving surface to wash away salts and other impurities, thereby desalting the sample applied to the receiving surface;
to thereby prepare a sample for MALDI-MS.

21. The method of claim 20, wherein prior to applying the sample to the receiving surface, the sample support plate is treated with a polar organic solvent.

22. The method of claim 21, wherein the polar organic solvent is selected from the group consisting of acetonitrile, methanol, and water/organic solvent mixtures.

23. The method of claim 22, wherein the polar organic solvent is acetonitrile.

24. The method of claim 20, wherein the adsorbent layer is washed with an aqueous solution to remove the salts from the adsorbent layer.

25. The method of claim 20, wherein the sample comprises an analyte of interest, a matrix material, one or more salts, and one or more solvents.

26. The method of claim 25, wherein the solvent is aqueous.

27. The method of claim 20, wherein the sample contains a solution of a matrix material.

28. The method of claim 20, wherein the sample does not contain a matrix material.

29. The method of claim 28, wherein the matrix material is added after the adsorbent layer is washed with an aqueous solution.

30. A method for preparing the sample support plate of claim 1 comprising:
providing a sample support plate comprising a sample presentation surface;
forming on the top sample presentation surface at least one receiving surface of an adsorbent layer, wherein the adsorbent layer retains selected molecules on the receiving surface.

31. The method of claims 30, wherein the adsorbent layer comprises a polymeric film.

32. The method of claim 31, further comprising
admixing a monomer, a polymer, or a combination thereof, a porogen, and an initiator;
coating the target spot with the admixture;
initiating a polymerization reaction to form a polymeric film; and
washing the polymeric film to remove residual monomer, porogen and initiator.

33. The method of claim 32, further comprising treating the polymer film with a polar organic solvent.

34. The method of claim 33, wherein the polar organic solvent is selected from the group consisting of acetonitrile, methanol, and water/organic solvent mixtures.

35. The method of claim 34, wherein the polar organic solvent is acetonitrile.

36. The method of claim 31, further comprising
admixing a monomer, a polymer, or a combination thereof, and an initiator;
coating the target spot with the admixture;
initiating a polymerization reaction to form a polymeric film; and washing the polymeric film to remove residual monomer or polymer, porogen, and initiator.

37. The method of claim 32, wherein the porogen is selected from the group consisting of aliphatic hydrocarbons, aromatic hydrocarbons, esters, alcohols, ketones, ether, and any combination thereof.

38. The method of claim 37, wherein the initiator is selected from the group consisting of benzoyl peroxide, lauroyl peroxide, peroxodisulfate, Vazo 52, Vazo 64, Vazo 67, Vazo 88, V70, and any combination thereof.

39. The method of claim 32, wherein the polymer is selected from the group consisting of polystyrene and polyvinylpyrrolidinone.

40. The method claim 32, wherein the monomer is selected from the group consisting of a monovinyl monomer, a polyvinyl monomer, and a mixture of monovinyl and polyvinyl monomers.

41. The method of claim 40, wherein the monovinyl monomer is selected from the group consisting of styrene, N-vinylpyrrolidone, methacrylate, vinylacetate, glycidyl methacrylate, and any combination thereof.

42. The method of claim 40, wherein the monovinyl monomer is N-vinylpyrrolidone.

43. The method of claim 40, wherein the polyvinyl monomer is selected from the group consisting of divinylbenzene, ethylene dimethacrylate, bis-acrylamide, divinylpyridine, ethylene dimethacrylate, hydroxyalkylene dimethacrylate, and any combination thereof.

44. The method of claim 40, wherein the polyvinyl monomer is divinylbenzene.

45. The method of claim 40, wherein the mixture of monovinyl monomer and polyvinyl monomer is divinylbenzene and N-vinylpyrrolidone.

46. A method for preparing the sample support plate of claim 1 comprising:
forming, on a sample support plate having a sample presentation surface, at least one receiving surface of an adsorbent layer, wherein the adsorbent layer retains selected molecules on the receiving surface.

47. A plate or method of claim 1, wherein the presentation surface comprises at least one sample target spot, wherein the target spot comprises the adsorbent layer.

48. A method for performing Matrix-Assisted Laser Desorption/Ionization Mass Spectrometry (MALDI-MS) on an analyte of interest, comprising:
providing a sample support plate comprising a sample presentation surface, wherein the sample presentation surface comprises at least one receiving surface of an adsorbent layer comprising a polymeric film, wherein the adsorbent layer retains selected molecules on the receiving surface;
applying a sample comprising an analyte of interest to the receiving surface of the adsorbent layer;
allowing the analyte of interest in the sample to be retained on the adsorbent layer;
washing the adsorbent layer with an aqueous solution to remove the salts from the adsorbent layer, thereby desalting the sample; and
performing MALDI-MS on the desalted analyte of interest retained on the adsorbent layer.

* * * * *